(12) United States Patent
Schirm

(10) Patent No.: US 9,784,604 B2
(45) Date of Patent: Oct. 10, 2017

(54) METHOD FOR DETERMINING AT LEAST ONE GAS PARAMETER OF A FLOWING GAS

(71) Applicant: DIEHL METERING GMBH, Ansbach (DE)

(72) Inventor: Christian Schirm, Ansbach (DE)

(73) Assignee: HYDROMETER GMBH, Ansbach (DE)

( * ) Notice: Subject to any disclaimer, the term of this patent is extended or adjusted under 35 U.S.C. 154(b) by 465 days.

(21) Appl. No.: 14/306,586

(22) Filed: Jun. 17, 2014

(65) Prior Publication Data

US 2014/0373621 A1 Dec. 25, 2014

(30) Foreign Application Priority Data

Jun. 20, 2013 (DE) .......................... 10 2013 010 340
Jan. 23, 2014 (DE) .......................... 10 2014 000 939

(51) Int. Cl.

| | | |
|---|---|---|
| *G01F 1/68* | (2006.01) | |
| *G01F 1/684* | (2006.01) | |
| *G01N 25/18* | (2006.01) | |
| *G01N 27/18* | (2006.01) | |
| *G01N 33/00* | (2006.01) | |
| *G01F 1/696* | (2006.01) | |

(52) U.S. Cl.
CPC ............ *G01F 1/684* (2013.01); *G01F 1/6965* (2013.01); *G01N 25/18* (2013.01); *G01N 27/18* (2013.01); *G01N 33/0031* (2013.01)

(58) Field of Classification Search
USPC ............... 73/204.11, 204.19, 204.22, 204.23
See application file for complete search history.

(56) References Cited

U.S. PATENT DOCUMENTS 3,399,053 A * 8/1968 Nievelstein ............... C22B 1/02
266/178
5,836,693 A * 11/1998 Stulen ................... G01F 1/6847
374/138

(Continued)

FOREIGN PATENT DOCUMENTS

DE 102007050792 A1 5/2008

*Primary Examiner* — Clayton E Laballe
*Assistant Examiner* — Warren K Fenwick
(74) *Attorney, Agent, or Firm* — Scully Scott Murphy and Presser

(57) ABSTRACT

A method for determining at least one gas parameter, of a flowing gas, by means of a flow meter, comprising a measurement section having a heating element and at least three temperature sensors, over which the gas is fed, at least one first temperature sensor being arranged upstream of the heating element, at least one second temperature sensor being arranged in the region of the heating element, and at least one third temperature sensor being arranged downstream of the heating element, wherein a calculation unit determines the at least one gas parameter as a function of the temperature measurement values at the first, second and third temperature sensors, and/or at least two separate gas parameters as a function of the temperature measurement values of individual different temperature sensors and/or the combinations of temperature measurement values of different temperature sensors.

26 Claims, 3 Drawing Sheets

(56) References Cited

U.S. PATENT DOCUMENTS

| | | | |
|---|---|---|---|
| 7,399,118 B2* | 7/2008 | Matter | G01F 1/6965 374/31 |
| 7,644,613 B2 | 1/2010 | Mayer et al. | |
| 2012/0029786 A1* | 2/2012 | Calandra | F01D 25/02 701/100 |
| 2013/0074593 A1* | 3/2013 | Eto | G01F 1/698 73/204.11 |
| 2014/0250857 A1* | 9/2014 | Kajita | B01D 53/864 60/39.5 |
| 2014/0352423 A1* | 12/2014 | Kurz | G01F 1/684 73/204.11 |
| 2015/0316401 A1* | 11/2015 | Popp | G01N 25/18 73/204.11 |
| 2016/0011028 A1* | 1/2016 | Skarping | G01F 1/6965 73/204.11 |

* cited by examiner

METHOD FOR DETERMINING AT LEAST ONE GAS PARAMETER OF A FLOWING GAS

BACKGROUND OF THE INVENTION

The invention relates to a method for determining at least one gas parameter, in particular a flow quantity, of a flowing gas, by means of a flow meter, comprising a measurement section having a heating element and at least three temperature sensors, over which the gas is fed, at least one first temperature sensor being arranged upstream of the heating element, at least one second temperature sensor being arranged in the region of the heating element, and at least one third temperature sensor being arranged downstream of the heating element, in particular with the heating element itself being usable as a temperature sensor.

DISCUSSION OF THE PRIOR ART

One method for measuring the flow quantity and further parameters of a gas flowing through a measurement section is to heat the gas in a region of the measurement section and then, for example, to determine the flow quantity of the gas with the aid of temperature data of one temperature sensor arranged upstream and one temperature sensor arranged downstream. If there is no gas flow, and the temperature sensors arranged upstream and downstream are equally far away from the heating element, the same temperature will be measured at the two temperature sensors. With increasing gas flow over the temperature sensors and the heating element, directed transport of the heated gas takes place from the heating element in the direction of the arranged temperature sensor downstream. An increasing gas flow therefore leads to an increasing asymmetry of the temperature distribution and therefore an increasing temperature difference which is measured with the two temperature sensors.

However, the measured temperature difference does not depend exclusively on the gas flow quantity, but also on further parameters such as the ambient temperature, which determines the medium temperature and therefore the temperature reference point, and the parameters of the gas flowing through the measurement section, or of the composition of a gas mixture flowing through the measurement section. With the described type of detection of a flow, quantitative results with high accuracy can thus be obtained only when at least the ambient temperature and the type or composition of the gas is known.

Particularly when measuring the flow of natural gases, however, the composition of the gas flowing through the flow meter may change. In this case, it is necessary to correct the data obtained according to the type of gas or the gas composition. To this end, further parameters of the gas flowing through the measurement section need to be determined.

In order to determine further gas parameters, at least two temperature sensors may be used on each side of the heating element, so that additional information about the temperature distribution can be obtained. As an alternative or in addition, the temperature value of at least one temperature sensor may also be measured under two different conditions, for example once with a gas flow and once with a stationary gas, or the like. In this way, it is additionally possible to determine the thermal conductivity of a gas, so that compensation of the flow measurement is possible for certain groups of gases.

The described methods can only determine one additional gas parameter, however, so that calibrations are still possible only for a few gas mixtures.

SUMMARY OF THE INVENTION

It is therefore an object of the invention to provide a method for determining at least one gas parameter, which permits the use of relatively simple sensors and furthermore allows accurate determination of additional gas parameters for a multiplicity of gas types.

With a method of the type mentioned in the introduction, the object is achieved according to the invention in that a calculation unit determines the at least one gas parameter as a function of the temperature measurement values at the first, second and third temperature sensors, and/or in that the calculation unit determines at least two separate gas parameters as a function of the temperature measurement values of individual different temperature sensors and/or the combinations of temperature measurement values of different temperature sensors, the temperature measurement values at the first, second and third temperature sensors being used in the scope of the determination of the gas parameters.

The invention is based on the idea of using at least one second temperature sensor at the heating element in addition to the temperature sensors placed upstream and downstream of the heating element. It is known to use a temperature sensor at the heating element for diagnostic purposes of the flow meter. In the method according to the invention, conversely, the temperature value at the temperature sensor in the region of the heating element is intended to be used in the determination of at least one gas parameter, in which case, in particular, the heating element itself may be used as a second temperature sensor. Thus, in the method according to the invention, the temperature values of three temperature sensors are determined and all three of these temperature values are used in the scope of the determination of one or more gas parameters.

In the simplest case, the temperature values of all three temperature sensors may be used in order to determine a single gas parameter. This is possible, for example, by compiling, in preparatory measurements a three-dimensional look-up table which comprises calibration values that indicate the gas parameter as a function of all three temperature measurement values.

For example, a flow quantity which depends on all three temperature values may be determined by using such a look-up table. Of course, it is also possible to determine a plurality of parameters from the three temperature measurement values with a plurality of such look-up tables; for example, a thermal conductivity or thermal diffusivity may also be determined. It is also possible for such tables to contain information about gas compositions or gas types.

Instead of using look-up tables, it is of course also possible, for example, to express the dependency of the gas parameter on the temperature values by a weighted sum of the temperature values of the temperature sensors. Such a weighted sum may be regarded as a linear approximation of the three-dimensional dependency of a gas parameter. Furthermore, it is also possible to add other sum components, which depend for example on the product of two temperature measurement values, a power of a temperature measurement value, or the like. A great advantage of the use of weighted sums over the use of multidimensional look-up tables is that the storage consumption in the calculation unit of the flow meter is substantially less, which is advantageous since calculation units that are as simple as possible should be used for flow meters.

It is in this case also possible for the calculation unit to be provided with temperature values which have already been preprocessed. For example, it is possible to provide an electronic switching unit which connects the temperature sensors in such a way that an output signal of the switching unit depends on temperature measurement values of a plurality of temperature sensors. In this case, for example, simple analogue addition or subtraction circuits may be used in order to provide linear combinations of the temperature measurement values, or output signals, of a plurality of temperature sensors, in an already preprocessed fashion.

The determination of the aforementioned three-dimensional calibration table for the determination of a gas parameter, or the finding of a formula which describes a group of gases well, can be very demanding. For this reason, it is also possible for the calculation unit to determine at least two separate gas parameters. For example, a thermal conductivity and/or thermal diffusivity of the gas may be determined in addition to the flow quantity. This can be particularly straightforwardly possible when particular gas parameters can be assigned to particular independent combinations of the temperature measurement values at the temperature sensors. In this case, for example, a sum of or a difference between, two temperature measurement values may be used in order to indicate a value in a one-dimensional calibration table, which is then read, particularly in an interpolated fashion. Since only one-dimensional calibration tables are present in this case, calibration of a flow meter is substantially more straightforwardly possible.

Conventionally, at least one of the gas parameters will depend on at least two of the temperature measurement values. Since three measurement values of three temperature sensors are available, three independent physical parameters of the gas can be determined. These may for example be the gas flow, the thermal diffusivity and the thermal conductivity. The determination of these parameters will be explained below by way of example.

The flow quantity may, as explained in the introduction, be determined from the asymmetry of the temperature distribution at the three temperature sensors. Such an asymmetry may, for example, be expressed by the temperature difference of the first and third temperature sensors being determined as a measurement value for the gas flow. Such a difference may be determined by acquiring two separate temperature measurement values and subsequently subtracting the temperature values in the calculation unit.

With an increasingly larger gas flow, increasingly more heated gas is transported from the heating element to the third temperature sensor, so that the temperature measurement value at the third temperature sensor increases, although the temperature decreases again with a flow increasing further. Owing to the opposing gas flow, it becomes increasingly more difficult for the gas to diffuse from the heating element to the first temperature sensor. The gas flow therefore forms a monotonic function, in particular a root function, of the temperature difference between the temperature at the third temperature sensor and the temperature at the second temperature sensor. In order to take into account nonlinearities of this dependency, and the dependency on further parameters, a calibration table may for example be used.

The thermal diffusivity of the gas may, for example, be extracted from the width of the temperature distribution. If the thermal diffusivity of the gas is high, then an elevated temperature is still measured further away from the heating element. This broadening of the curve may, for example, be determined by considering the sum of the temperature measurement values at the first temperature measurement sensor and the third temperature measurement sensor. If the sum of these two temperature measurement values is large, then the temperature distribution is broad, which in turn corresponds to a high thermal diffusivity. As previously in the determination of the gas flow from the asymmetry, a look-up table with calibration values may also be used for determining the thermal diffusivity from the width of the curve.

As a last gas parameter, for example, the thermal conductivity of the gas flowing through the measurement section may be determined. In the method according to the invention, unregulated heating of the heating element is usually carried out. If the thermal conductivity of the gas flowing through the measurement section is then high, this means that a large amount of energy is transported away from the heating element. The temperature at the heating element therefore decreases, when it is heated with the same heating power. A high temperature at the second temperature sensor thus corresponds to a low thermal conductivity, and a low temperature corresponds to a high thermal conductivity. In this case, the temperature value at the second temperature sensor may thus be used directly as the relevant value for determining the thermal conductivity. As above for the determination of the gas flow and the thermal diffusivity, the determination of the parameter may be carried out here by using a look-up table with calibration values.

As mentioned in the introduction, the use of three temperature sensors makes it possible to determine three independent gas parameters. The fact that the gas parameters are independent in the gas parameter determination described above can readily be seen from the fact that the respective characteristic quantities, i.e. the difference in the temperature values at the first and third temperature sensors, the sum of the temperature values at the first and third temperature sensors, and the temperature at the second temperature sensor, are linearly independent linear combinations of the temperature values at the temperature sensors. This means that the corresponding characteristic measurement quantities are also linearly independent. A change in one of the quantities therefore does not automatically lead to a change in another of the quantities. The quantities are therefore independent.

Often, in a flow meter, a further temperature sensor is provided which measures the ambient temperature, or the temperature of the gas, which is far away from the heating element. This was not mentioned in the explanation above, since the ambient temperature or gas temperature can be determined directly as an independent parameter.

When determining a plurality of gas parameters, it is particularly advantageous that the values of one gas parameter can be corrected as a function of at least one further parameter. As explained, the gas flow is dependent on the asymmetry of the temperature distribution and also on the thermal diffusivity and the thermal conductivity. Yet since these further quantities can be measured in the method according to the invention, correction of the initially determined gas flow is therefore also possible. Such correction can only be carried out in one direction, that is to say, for example, a gas flow which has been determined is corrected as a function of a thermal diffusivity and/or thermal conductivity which has been determined, although the correction may also be carried out self-consistently, that is to say the gas flow is initially corrected by one or both of the other parameters and the further parameters are subsequently corrected by the gas flow, etc.

As already explained by way of example, as a function of the temperature measurement values of the at least three temperature sensors, it is possible to determine three independent gas parameters which are determined by the calculation unit as a function of three linearly independent linear combinations of the temperature measurement values of the first, second and third temperature sensors. Such a linear combination is typically calculated as a weighted sum, in which case the weightings may also be negative. This is advantageous in particular when, in the weighting for calculating at least one parameter, in particular at least two parameters, the weight of two temperature measurement values is not equal to zero.

Furthermore, the ambient temperature and/or the gas temperature outside the measurement region of the at least three temperature sensors and at a distance from the heating element, in particular before entry of the gas into the measurement region of the first temperature sensor and/or after emerging from the measurement region of the third temperature sensor, may be measured by at least one fourth temperature sensor. It is therefore possible to take into account the temperature of the surroundings, or of the gas, at a distance from the heating element, in the calculation of the gas parameters. In particular, this temperature may be regarded as an independent parameter, although it may also be linked with the temperature values of the three temperature sensors.

It is furthermore possible that, when at least two gas parameters are being determined, the gas parameters are determined repeatedly, the determination being repeated with a different time interval for at least one of the gas parameters than for at least one other of the gas parameters. Often, it is desirable for a flow meter to operate as economically as possible. Unnecessary measurement and calculation processes should therefore be avoided. If it is then to be expected that one of the gas parameters, for example a composition of the gas, changes very much more slowly than another of the gas parameters, for example the flow quantity, then the more rapidly varying parameter may be measured with a short time interval, for example every second or several times per second, while the slowly varying parameter is measured at an interval of several seconds or even minutes. Since no variations, or only slight variations, are to be expected for the slowly varying parameter between the measurements of the rapidly varying parameter, the previously measured measurement value of the slowly varying gas parameter can nevertheless still be used for correcting the values determined for the more rapidly varying gas parameter.

Often, a flow quantity is intended to be determined as a gas parameter of the flow meter. In this case, an uncorrected flow quantity may be determined as one of the gas parameters from temperature measurement values at the first and third temperature sensors, a corrected flow quantity being determined from the uncorrected flow quantity and at least one other of the gas parameters which have been determined.

In particular, at least one of the gas parameters determined may describe a thermal conductivity of the gas or a thermal diffusivity of the gas. As explained in the introduction, a thermal conductivity may, for example, be determined by as a function of the temperature measurement value of the second temperature sensor, and a thermal diffusivity may be determined as a function of the sum of the measurement values of the first and third temperature measurement sensors, or from the individual values of these temperature measurement sensors.

Often, in gases, there is an interaction between several of the measured gas parameters. For example, a thermal conductivity and/or a thermal diffusivity may have an effect on the symmetry relationship of the temperature distribution and the flow quantity. In the simplest case, this can be corrected by taking into account values determined for further gas parameters when determining a gas parameter. For example, it is possible to change and/or interpolate between a plurality of look-up tables with calibration values, although simple additive correction factors or the like may also be used.

It is possible for a corrected gas parameter describing a thermal conductivity to be determined as one of the gas parameters as a function of an uncorrected gas parameter describing a thermal conductivity and a gas parameter describing a flow quantity. By this compensation, it is possible to correct an effect of the flow quantity and therefore also of the average flow speed on the thermal conductivity which is determined.

A correction of a gas parameter, or a determination of a gas parameter, is in this case of course also possible as a function of a plurality of previously determined gas parameters, or those temperature measurement values from which these gas parameters are determined. In this case, the gas parameters used for the determination or correction may already have been determined beforehand, in which case, in particular, for determining these gas parameters it is possible to use temperature measurement values determined at a different time than for determining the gas parameter to be determined, or corrected. As an alternative, however, it is also possible to use the measurement values of the at least three temperature sensors at precisely one instant for determining both those gas parameters which are used for the correction or determination and the gas parameter which is corrected, or determined.

In this case, it is possible in particular for a gas parameter describing a thermal diffusivity to be determined as one of the gas parameters as a function of a gas parameter describing a thermal conductivity and a gas parameter describing a flow quantity, each of which is determined as a function of at least one instantaneous or previously acquired temperature measurement value.

Since a dependency between gas parameters is often reciprocal, that is to say, for example, a flow quantity which is determined depends on the actual thermal diffusivity and a thermal diffusivity which is determined depends on the actual flow quantity, a correction of the values may be carried out by an iterative method. It is therefore possible to determine at least two of the gas parameters by an iterative method, with, alternately, at least one first of the gas parameters being determined in a first step as a function of at least one second of the gas parameters, and in particular as a function of the temperature measurement value at at least one of the temperature sensors, and at least the second of the gas parameters being determined in a second step as a function of the first of the gas parameters, and in particular as a function of the temperature measurement value at the temperature sensor or at at least one other of the temperature sensors.

In such an iterative method, it is possible for temperature measurement values at the temperature sensors to be determined only at the start of the method. It is, however, also possible to take into account the current temperature measurement values of the temperature sensors in each of the iteration steps, or at least in the iteration steps in which a first of the parameters is adapted.

As explained, the relationship between a gas parameter to be determined and the temperature value used therefor, or the combination of temperature values used therefor, is often nonlinear and dependent on the type of gas, or the like. It is therefore possible to use a look-up table, in particular a multidimensional look-up table, the values of which are read, particularly in an interpolated fashion, as a function of the temperature measurement value, assigned respectively to a dimension of the look-up table, of at least one of the temperature sensors, in order to determine the gas parameter or at least one of the gas parameters. Such look-up tables may be determined during calibration of the flow meter before use to determine gas parameters.

In the simplest case, a multiplicity of gases or gas mixtures with known parameters may be fed with a multiplicity of flow speeds through the flow meter, and the temperature values at the temperature sensors may respectively be determined during this. For a multiplicity of gases, a relationship is in this case determined, with which, for each combination of temperature measurement values, a particular value of a gas parameter can be determined. Such a value may also be a gas type, the proportion of a gas in a gas mixture, or a gas mixture itself. Thus, the entries in these tables may not exclusively be numerical values. Alphanumeric information, or values which are assigned to alphanumeric information, may also be stored directly in the look-up tables.

However, it is also possible that the temperature measurement values of the temperature sensors do not determine the gas parameter or at least one of the gas parameters uniquely, so that with the same temperature measurement values of all the temperature sensors a plurality of different values are determined for the gas parameter, the selection of the value determined being dependent on preceding temperature measurement values of at least one of the temperature sensors and/or preceding values of the same gas parameter or another of the gas parameters and/or known operating conditions of the flow meter, in particular information about gas compositions to be expected.

In particular, the flow meter may be calibrated for a multiplicity of gases and/or gas mixtures, that is to say gas parameters are intended to be determined for large groups of gases or gas mixtures. In this case, it is possible that a unique value cannot be assigned to one or more of the gas parameters for a combination of temperatures determined at the temperature sensors. For example, it is possible that, depending on the gas mixture which flows through the flow meter, a certain temperature distribution corresponds to a large flow in the case of a high thermal diffusivity, but similar values are measured for another gas with a smaller gas flow, for example because the thermal diffusivity is less and other unmeasured gas parameters likewise differ.

In these cases, it is possible in particular to carry out a consistency check of the gas parameters. For example, it may be known that certain gases are not contained in the gas mixture, so that some of the values can be excluded. The calculation unit itself may already carry out a consistency check without additional external information in that previously determined gas parameters, or values at temperature sensors, are taken into account when determining the gas parameters. For example, it is much more likely that a gas composition changes only slightly than that an entirely different gas composition suddenly flows through the flow meter.

In the scope of such a consistency check, it is possible to fully discard some of the possible gas parameters, particularly when it is determined that the probability lies below a predetermined limit value. It is, however, also possible to form the value of the gas parameter as a weighted sum of the various possible values of the gas parameter, the weighting factors being dependent on the probability of the correctness of the value of the gas parameter.

As mentioned, it may often be disadvantageous to use large look-up tables for determining gas parameters, since calculation units with very limited resources are often used in flow meters. It may therefore be advantageous for the dependency of the gas parameter on the temperature values at the temperature sensors to be approximated by linear or polynomial approximations in order to calculate the gas parameter. For example, an uncorrected flow may be calculated directly from the difference between the first and third temperature sensors, in which case this difference may be scaled and an offset may be added to the scaled difference. The scaling and the offset may, in particular, be dependent on further gas parameters which are determined. If it is known of a gas parameter that it cannot be expressed sufficiently accurately over the entire value range by such an approximation, then it is also possible to use polynomial approximations in which, for example, powers of the differences or sums of temperature measurement values are taken into account. Higher powers of temperature measurement values or the products of different temperature measurement values are thus used in the calculation of the gas parameter.

The gas parameter or one of the gas parameters may also be a mixing ratio of at least two gases, a concentration of a gas type, or the gas type of a gas. This is possible particularly when it is known that only a small group of gases can flow through the measurement section. The determination of the said parameters is advantageous in particular since in this case, for example depending on the type of gas, different calculation methods can be used for the further gas parameters, or the like. Furthermore, by determining the gas type or the mixing ratio, it is also possible to determine further parameters of the gas which cannot be determined directly in the flow meter itself. For example, it is possible to determine a calorific value of a gas, so that it is then possible, for example, to derive the gas quantities according to the actual calorific value instead of a pure volume derivation.

In order to obtain further information about the gas flowing through the flow meter and to determine gas parameters more accurately, or to determine further gas parameters, the conditions under which the temperature measurement values are determined may also be modified. In this case, in particular, the heating power of the heating element may be varied between a first value and at least one second value in order to determine at least one further independent gas parameter.

In particular, a temperature measurement value of at least one temperature sensor, or a value derived therefrom, may be determined at a time at which the heating element is switched off, at least one gas parameter being determined as a function of this temperature measurement value.

In the method according to the invention, additional information about the gas is provided by evaluating temperature measurement values of at least three temperature sensors. In this case, particularly in the case of a known qualitative composition of the gas, it may be particularly advantageous for a calorific value of the gas to be determined as the gas parameter or at least one of the gas parameters. The combination of a calorific value determination with a determination of the flow quantity makes it possible, in particular, to carry out calculation of a delivered gas quantity not exclusively according to the volume of the gas provided, but according to the total calorific value of the gas provided.

The invention furthermore relates to a flow meter, comprising a calculation unit and a measurement section having a heating element and at least three temperature sensors, over which the gas is fed, at least one first temperature sensor being arranged upstream of the heating element, at least one second temperature sensor being arranged in the region of the heating sensor, and at least one third temperature sensor being arranged downstream of the heating element, the second temperature sensor being formed in particular by the heating element, and the calculation unit being formed in order to carry out the method described above.

The flow meter may, in particular, comprise a plurality of second temperature sensors, which are arranged upstream and downstream directly next to the heating element and provide a temperature measurement value individually or together. In addition or as an alternative, the flow meter may also comprise a plurality of first temperature sensors and/or a plurality of third temperature sensors, which respectively provide temperature measurement values individually or together. By using a plurality of temperature sensors, the measurement quality can be improved. In particular, by a symmetrical arrangement of two second temperature sensors with respect to the heating element, it is particularly readily possible to carry out temperature measurements for the region of the heating element without having to arrange the temperature sensor directly at the heating element itself.

In the flow meter according to the invention, the temperature values of the temperature sensors may in particular be acquired directly and subjected to analogue/digital conversion, in which case the subsequent further processing and combination of the temperature measurement values for determining the gas parameters may be carried out entirely digitally. However, it is of course also possible to carry out the combination of the temperature measurement values at least partially by separate analogue or digital circuits. In particular, it is possible for the flow meter to comprise an electronic switching unit which connects the first temperature sensor or at least one of the first temperature sensors to the second temperature sensor or at least one of the second temperature sensors and/or to the third temperature sensor or at least one of the third temperature sensors, or the second temperature sensor or at least one of the second temperature sensors to the third temperature sensor or at least one of the third temperature sensors, in such a way that at least one output signal of the switching unit depends on the linearly, in particular by addition or subtraction and/or by multiplication and/or by division, combined temperature measurement values of the temperature sensors connected by the switching unit, the calculation unit being formed in order to determine the gas parameter or at least one of the gas parameters as a function of the output signal of the switching unit.

BRIEF DESCRIPTION OF THE DRAWINGS

Other advantages and details of the invention may be found in the following exemplary embodiments and the associated drawings, in which.

DETAILED DESCRIPTION OF THE INVENTION

Figure 1:
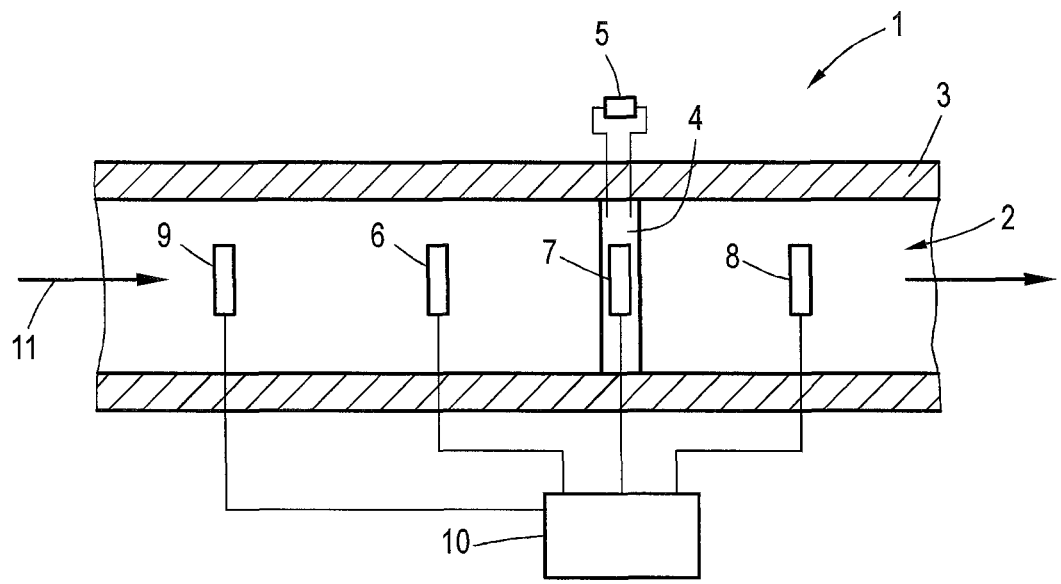
FIG. 1 schematically shows an exemplary embodiment of a flow meter according to the invention, FIG. 2 schematically shows the sequence of one exemplary embodiment of a method according to the invention, FIG. 3 schematically shows the sequence of another exemplary embodiment of a method according to the invention, FIG. 4 schematically shows the sequence of a third exemplary embodiment of a method according to the invention, FIG. 5 schematically shows the sequence of a fourth exemplary embodiment of a method according to the invention, FIG. 6 schematically shows the sequence of a fifth exemplary embodiment of a method according to the invention.

FIG. 1 shows an exemplary embodiment of a flow meter for determining at least one gas parameter. The flow meter 1 comprises a measurement section 2, which is located inside a pipe 3. Here, for example, the pipe 3 is formed as a rectangular pipe with a small height, in order to generate laminar flow.

Arranged centrally inside the measurement section 2, there is a heating element 4 which can be controlled by a controller 5. The controller 5 may be formed as a separate controller, although it may also be controllable by the calculation unit 10. The driving of the heating element 4 by the controller 5 is typically carried out in such a way that the heating power of the heating element 4 is constant. In order to obtain further information about the gas which flows through the measurement section 2, the heating power of the heating element 4 may however also be varied between two or more values by the controller 5. If the heating element 4 has an almost constant resistance over a wide temperature range, it may be sufficient to supply it with a constant voltage or a constant current by the controller 5 in order to achieve a constant heating power. It is, however, also possible for the controller 5 to regulate the heating power to a constant value.

Besides the heating element 4, three temperature sensors 6, 7 and 8 are arranged in the measurement section 2. The temperature sensor 7 is arranged in the region of the heating element 4. The two temperature sensors 6, 8 are respectively arranged upstream and downstream of the heating element. The arrows 11 indicate the flow direction of the gas. The measurement values of the temperature sensors 6, 7 and 8 are acquired by the calculation unit 10. This may, for example, be carried out via analogue/digital conversion. Furthermore, a further temperature sensor 9 which measures the ambient temperature is arranged in the gas flow, but much further away from the heating element 4 than the temperature sensors 6, 8. The ambient temperature corresponds approximately to the temperature of the gas flowing in, and can therefore be used to make the gas parameters which have been determined more precise.

The calculation unit 10 acquires the temperatures at the temperature sensors 6, 7, 8 and 9, and determines one or more gas parameters from the temperature values at the temperature sensors 6, 7, 8 and 9; it uses at least the temperature values at the temperature sensors 6, 7 and 8 in order to determine the gas parameters. The evaluation of the temperature values at the temperature sensors 6, 7 and 8 will be described below with reference to FIG. 2 to FIG. 6.

Figure 2:
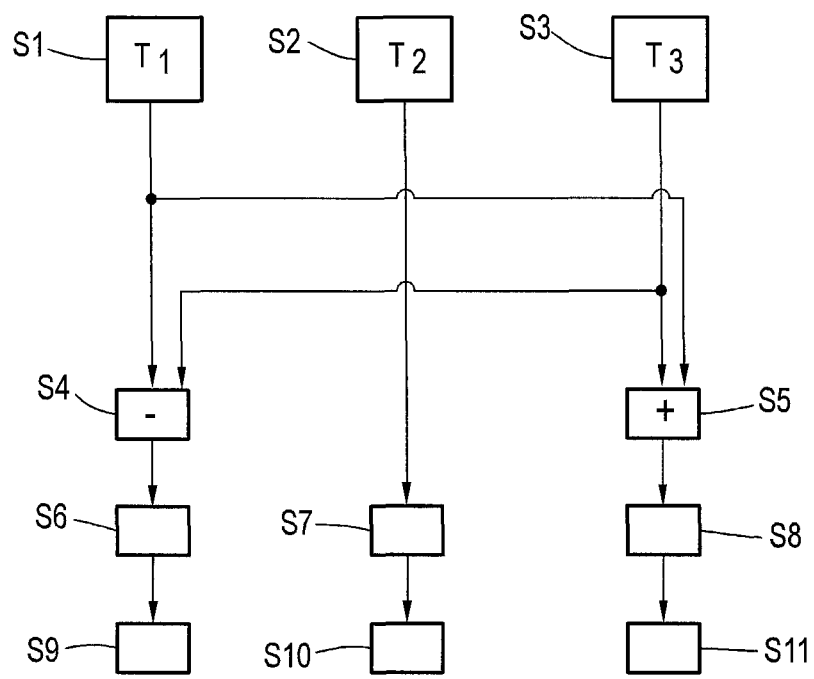

FIG. 2 shows by way of example a possible way of determining gas parameters from the temperature values of the temperature sensors 6, 7 and 8 shown in FIG. 1. In the steps S1, S2 and S3 carried out simultaneously or at a short time interval, the temperature value T1 at the temperature sensor 6, the temperature value T2 at the temperature sensor 7 and the temperature value T3 at the temperature sensor 8 are acquired. For further processing of these values, the fact that different flow quantities and different further gas parameters lead to a different temperature distribution inside the measurement section 2 is used. The temperature will typically fall back to the ambient temperature as a bell-shaped distribution around the heating element 4. From the height, width and asymmetry of the temperature distribution, however, it is possible to determine essential gas parameters. For example, the flow quantity can be determined from the asymmetry of the temperature distribution. If scarcely any gas is flowing through the measurement section 2, then the temperature should decrease uniformly in both directions from the heating element 4, so that the temperature should be approximately the same at the temperature sensors 6 and 8 lying equally far away from the heating element. If gas is flowing through the measurement section 2, however, the effect of this is that warm air is displaced from the heating element 4 in the direction of the temperature sensor 8. The result of this is that the temperature value T3 at the temperature sensor 8 is raised. If the flow increases further, the temperature value T3 decreases again. At the same time, less warm air can diffuse from the heating element 4 to the temperature sensor 6, for which reason the temperature T1 at the temperature sensor 8 decreases.

In order to calculate the gas flow, in step S4 the temperature value T1 may therefore be subtracted from the temperature value T3. The difference in the temperature values T1 and T3 at the temperature sensors 6 and 8 is a good measure of the asymmetry of the temperature distribution of the gas. This difference therefore also forms a good measure of the flow quantity.

In order to take into account nonlinearities and offsets of this dependency, in step S6 the difference value determined in step S4 may be used as an index for reading a look-up table. As an alternative, in step S6 it is also possible to provide the difference value determined in step S4 with an offset and scale it, or to add further higher-order factors, for example the square of the difference, or the like.

The further processing in step S6 of the difference value determined in step S4 is also used, in particular, for output or storage, to determine values in step S9 which are indicated in conventional units, for example $cm^3/s$, or the like. The scaling and offset factors used in step S6, or the look-up table used therein, may be established in the scope of the calibration of the flow meter.

In the exemplary embodiment shown, it is firstly assumed that the processing in step S6 is always carried out in the same way. It should, however, already be pointed out that the processing in step S6 may also be dependent on the currently or previously measured further gas parameters or temperature values.

One further gas parameter, which may provide an indication of the gas types being measured, or may for example be used to correct the flow quantity calculated in step S6, is the thermal conductivity of the gas or gas mixture which flows through the measurement section 2. In the method shown, the heating element 4 is typically heated with a constant power. The temperature of the heating element 4, or the temperature T2 measured at the heating element 4 by the temperature sensor 7 in step S2, is therefore dependent on how rapidly heat can be transported away from the temperature sensor 4. If the thermal conductivity of a gas is high, then stronger heat transport can take place and the temperature T2 is lower than in the case in which the thermal conductivity is very low, and therefore scarcely any heat transport away from the heating element 4 takes place. The temperature T2 measured in step S2 can therefore be used directly as a measure of the thermal conductivity of the gas flowing through the measurement section 2, particularly when the gas is at rest.

The value measured in step S2 may be processed further in step S7 in order to take offsets and scalings into account, or a look-up table may be used in step S7 in order to take into account nonlinearities in the relationship between the temperature value T2 and the thermal conductivity. The comments regarding step S6 apply for the determination and use of these tables.

Subsequently, the value determined in step S7 may be output or stored in step S10. Here again, it is possible for the value which is determined to be corrected as a function of the further gas parameters which are determined, as will be explained in more detail below.

Besides the height of the temperature distribution which, as explained, is a measure of the thermal conductivity, and the asymmetry of the temperature distribution which, as explained, is a measure of the flow quantity, the width of the temperature distribution may also be determined The width of the temperature distribution may be regarded as a measure of how rapidly heat transport takes place in the gas, i.e. a measure of the thermal diffusivity. A greater width of the temperature distribution leads to the temperature values at the temperature sensors 6 and 8, i.e. the temperature values T1 and T3, rising. For example, the sum of the temperature values T1 and T3 may be considered as a measure of the width. This sum is formed in step S5 from the temperature values T1 and T3 measured in step S1 and step S3. Here again, further processing, for which the comments regarding step S6 and step S7 apply, is carried out in step S8. The value determined for the thermal diffusivity is output or stored in step S11.

Already with the method which has been presented and which is relatively straightforward to implement, additional gas parameters can be determined besides the flow quantity, namely for example the thermal diffusivity and the thermal conductivity. Besides direct representation or storage of these values in steps S9, S10 and S11, it is of course possible to correct the value of at least one of these gas parameters as a function of the further gas parameters which have been determined. It is also possible for the further gas parameters which have been determined to be taken into account already in the processing steps S6, S7 and S8. For example, in step S6 it is possible to select or interpolate between a plurality of look-up tables for calculation of the flow quantity, the selection or the interpolation point between the tables being dependent on the thermal conductivity and thermal diffusivity being determined Furthermore, the values of further sensors, for example the temperature value of the further temperature sensor 9, may likewise also be used in the calculation. These more complex combinations will be explained below with reference to the further figures.

Figure 3:
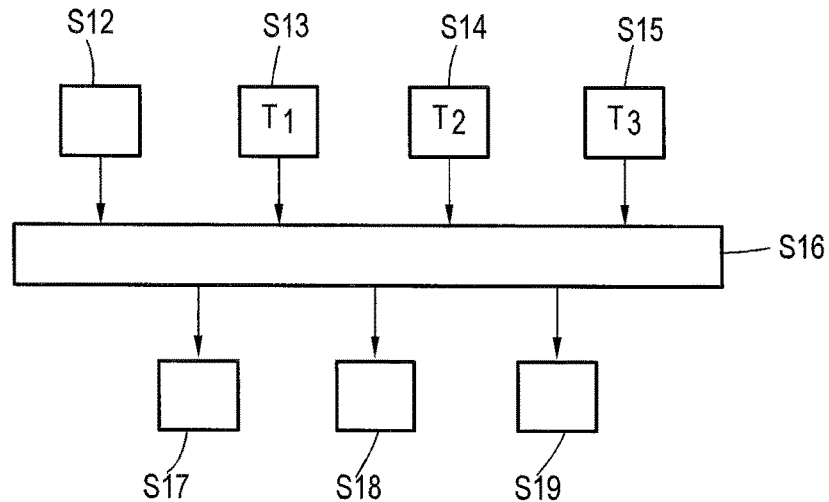

FIG. 3 shows, by way of example, a method in which one or more parameters are determined as a function of a plurality of measurement values. First, in steps S12, S13, S14 and S15, measurement values are determined. In steps S13, S14 and S15, the temperatures T1, T2 and T3 are determined, as already explained concerning steps S1 to S3. In step S12, the temperature value at the further temperature sensor 9 is also determined. Of course, other supplementary parameters, for example the temperatures at the temperature sensors 6, 7 and 8 in the event of a different heating power at the heating element, the temperature at a further temperature sensor which is arranged at a predetermined position in the measurement section, known values concerning gas compositions, or the like, may also be determined in step S12 or a further step. In steps S12 to S15, therefore, a plurality of parameters, in particular four parameters, are determined, which are subsequently used as indices for consultation in a multidimensional look-up table. For example, if the temperatures T1, T2, T3 and the temperature at the further temperature sensor 9 are used, then a four-dimensional look-up table is obtained for each gas parameter to be determined. For example, the determination of three gas parameters in steps S17, S18 and S19 is shown here. The principle will be explained only for the determination of a single gas parameter. Further gas parameters are determined equivalently.

If only a flow quantity is intended to be determined, for example, a look-up table, which has for example been determined during a calibration process of the flow meter 1, may be used therefor. For such a calibration process, a multiplicity of different gas types may flow through the flow meter 1 with different flow speeds and ambient conditions, the temperature values of the temperature sensors 6, 7 and 8 and the further temperature sensor respectively being acquired. For a multiplicity of gas groups, in this case it is possible to determine a unique determination of the flow quantity from the temperature values T1, T2 and T3 as well as the temperature at the further temperature sensor 9. In individual cases, however, it may be possible that the same temperature combination at the temperature sensors 6, 7, 8 and 9 has been established for different flow quantities during the calibration, for example when different gas compositions have been used. In order to resolve such ambiguities, in the measurement process it is possible for previous temperature measurement values, additional known parameters, for example the type of gas flowing through the flow meter, previously determined gas parameters, or the like, to also be used besides the currently measured temperature values T1, T2, T3.

Compared with conventional flow meters, by taking into account the temperatures T1, T2 and T3 as well as the further temperature sensor 9, significantly more accurate determination of the flow quantity is possible. The same also applies, of course, for other parameters. If a plurality of parameters are intended to be determined, a separate multidimensional look-up table is simply used for each of the parameters.

As an alternative or in addition to the determination of one or more parameters by using a look-up table, when determining a plurality of parameters from the temperature values T1, T2 and T3 and the temperature value of the further temperature sensor 9 it is also possible for one of the gas parameters to be determined as a function of a simultaneously or previously determined gas parameter. In this way, mutual dependencies between the gas parameters can be corrected. For example, a corrected gas parameter describing a thermal conductivity may be calculated by first determining an uncorrected gas parameter describing a thermal conductivity and a gas parameter describing a flow quantity, and by the corrected gas parameter being calculated as a function of these two parameters. As an alternative, it is also possible to determine a gas parameter as a function of a plurality of further gas parameters which have been determined. For example, a gas parameter describing a thermal diffusivity may be determined as a gas parameter, this being determined as a function of a gas parameter describing a thermal conductivity and a gas parameter describing a flow quantity.

Figure 4:
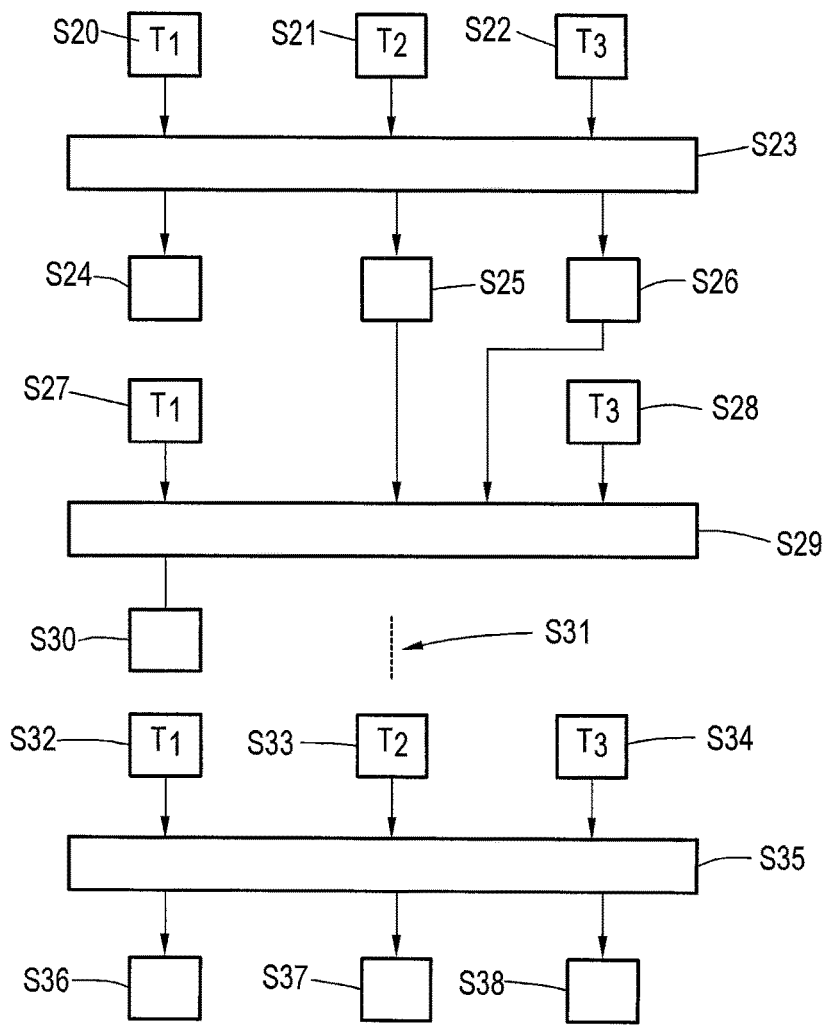

FIG. 4 shows a third exemplary embodiment for the determination of a flow, in which various gas parameters are measured with different frequencies. This is advantageous since the power consumption of a flow meter can be reduced in this way. In particular, gas meters are often supplied with energy by batteries or the like, and are intended to function for a long time without changing the batteries. Optimization of the electricity consumption of gas meters and other flow meters is therefore desirable. Steps S20 to S26 in this context show a first determination of three gas parameters. The determination of the three gas parameters is carried out essentially as shown in FIG. 3, although in this case only use of the temperature values T1, T2 and T3 is shown. Of course, this method may also be applied when the temperature values of a further temperature sensor 9 or further measurement values are used in the method. From the acquired temperature values T1, T2 and T3, by using three three-dimensional look-up tables in step S23 three gas parameters are determined, which are output, stored or the like in steps S24, S25 and S26. Of course, instead of a plurality of multidimensional look-up tables, in step 23 it is also possible to use simpler relationships between the temperature measurement values T1, T2 and T3 and the gas parameters, as explained for example in connection with FIG. 2.

If it is then assumed that one of the gas parameters, for example a flow quantity, changes significantly more rapidly than the other gas parameters, for example the thermal diffusivity and/or the thermal conductivity, and therefore the composition of the gas flowing through the flow meter 1, then it may be sufficient subsequently to measure one or more parameters, for example the flow quantity, repeatedly at a relatively short interval and only to determine the further gas parameters again after a longer time interval.

The determination of the more rapidly varying gas parameter is shown in steps S27 to S30. In steps S27 and S28, the temperature values T1 and T3 at the temperature sensors 6 and 8 are determined again. From these two temperature values, in step S29 a flow quantity may for example be determined, which is output, stored, or the like in step S30. It is possible for the determination in step S29 to be carried out only on the temperatures measured in step S27 and step S28. This may, for example, be done by determining a difference in the temperature measurement values T1 and T3 and appropriate further processing, as explained in connection with FIG. 2. It is also possible to use a two-dimensional look-up table.

However, it is also possible to use the further gas parameters determined in step S25 and step S26 for determining the flow quantity in step S29. Since it is assumed that these two gas parameters vary slowly, the parameters respectively determined may be used for a plurality of determinations of the flow quantity.

Steps S27 to S30 may be repeated several times. This is indicated as step S31. After multiple determination of the more rapidly varying gas parameter, however, the slowly varying gas parameters should be determined again, which is done in steps S32 to S38. This determination corresponds to the determination in steps S20 to S26.

In particular by using previously determined values for the slowly varying gas parameters, in the case of multiple determination of the rapidly varying gas parameter, a significant improvement in the accuracy of the determination of the rapidly varying gas parameter can be achieved without the slowly varying gas parameters having to be measured with the same frequency.

Figure 5:
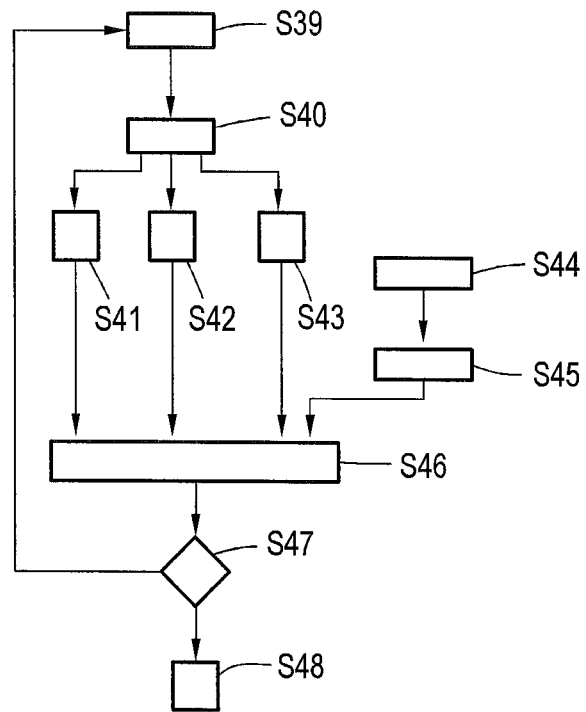

As already mentioned, it may be possible that, during the calibration of the flow meter, it is established that a plurality of values of one or more gas parameters lead to the same temperature values T1, T2 and T3 and the same values at further sensors. In such cases, which of the values is the correct value should be determined. An example of such determination is shown in FIG. 5. Here, in step S39, first all available measurement values, i.e. in particular the temperature values T1, T2 and T3, are acquired. In step S40, evaluation of these measurement values is carried out in order to determine at least one gas parameter. Various possibilities for this evaluation have already been explained with reference to FIGS. 2 to 4, and will also be explained with reference to FIG. 6. For greater clarity, only the determination of one gas parameter is represented in FIG. 5.

Now, it is possible that the gas parameter is not determined uniquely in step S40. Here, by way of example, the determination of three possible gas parameters in steps S41, S42 and S43 is shown. In order to resolve this ambiguity, it may be advantageous to obtain additional information. It is therefore possible for the heating element 4 to be heated with a different power in step S44 and for further values of the measurement parameters measured in step S40 to be acquired in step S45. The rest of the method is, however, also possible without these additional steps.

In step S46, an attempt is made to determine which of the gas parameters determined in steps S41, S42 and S43 is the correct gas parameter. In this case, it is possible to use the additional measurement values obtained after the heating, although it is also possible to use the values determined for further gas parameters or, for example, for there to be information, which can be used in this step, about possible gas compositions.

It is furthermore possible that previously determined values of the gas parameter or previously measured temperature values are stored and can be used in step S46 for determining the actual gas parameter. In step S47, a check is made as to whether it was possible to determine a unique parameter. If this is not the case, the method may be repeated from the start. In this way, parameters can be acquired over longer periods of time, so that it may be possible to distinguish between different possibilities for the gas parameter. If it is not possible to determine a value over a longer time, then an error may be output which indicates that further parameters are necessary for the evaluation, although an averaged value of the various possibilities for the gas parameter may also be formed. It is also possible, by using previous measurement values and additional measurement data and information, to determine probabilities for the various values of the gas parameter and to calculate the output or stored gas parameter determined in step S48 as a sum of these possible gas parameters weighted with the probabilities.

In the preceding exemplary embodiments, it was assumed that gas parameters are determined from an individual temperature value or a sum or difference of a plurality of temperature values, or that a multidimensional table is used for determining the gas parameter. The use of multidimensional tables requires large amounts of memory in the calculation unit, and the determination of such a multidimensional calibration table is demanding. On the other hand, direct determination of the gas parameters from individual temperature values or sums or differences of temperature parameters is often insufficient for achieving a desired accuracy. In some cases, it may therefore be advantageous initially to determine the gas parameters individually, but then to correct them as a function of the further gas parameters.

Since, typically, the values determined for a first gas parameter then depend on the actual values of a second gas parameter and the values determined for a second gas parameter depend on the actual values of a first gas parameter, there is a mutual dependency which cannot easily be resolved. It may therefore be advantageous to calculate the values of the gas parameters iteratively.

Figure 6:
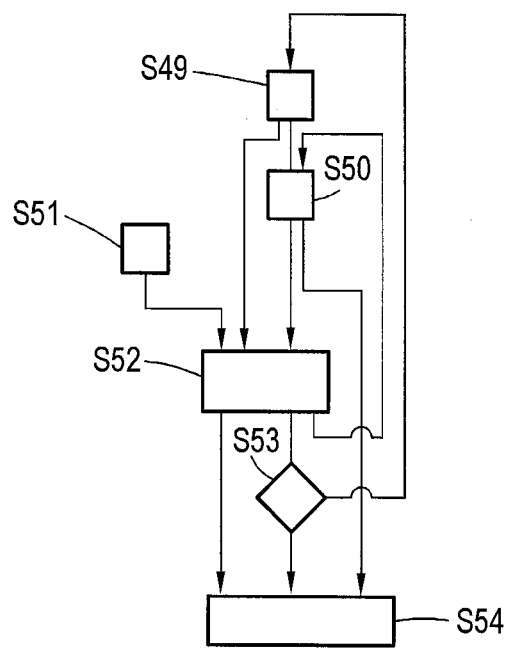

An example of such iterative calculation is shown in FIG. 6. Here, in step S49, one or more measurement values, in particular temperature measurement values T1, T2 and/or T3, are first acquired, from which a first gas parameter is determined in step S50. For example, such determination of a first gas parameter may be carried out here by a simple sum or difference of temperature values, as explained with reference to FIG. 2. After determination of the first gas parameter, further measurement values may be acquired in step S51. These may be current values of the temperature sensors already read in step S49, although it is also possible to read other temperature sensors or to use further values. In step S52, a second gas parameter is then determined. In order to determine the second gas parameter, on the one hand the values newly acquired in step S52 may be used, and on the other hand the values already acquired in step S49 may be used. In addition, the value of the first gas parameter which was determined in step S50 is taken into account in the determination of the second gas parameter in step S52. In step S52, a second gas parameter is thus determined from measurement values and a first gas parameter.

In step S53 a termination determination may be checked, which may for example be a convergence criterion, for example that two values consecutively determined for a gas parameter do not exceed a certain maximum difference. If this convergence criterion is not satisfied, then the method is repeated from step S49, although in step S50, in addition to the calculation of the first gas parameter, the second gas parameter determined in step S52 in the previous iteration is used. It is furthermore also possible to use the temperature measurement values of preceding iterations. As soon as the convergence criterion is satisfied in step S53, the first and second gas parameters determined last are output in step S54.

Clearly, this method may also be extended to the determination of further gas parameters; for example, a plurality of gas parameters may be determined in step S50 and/or in step S52.

The determination method described with reference to FIG. 6 is a self-consistent method, that is to say a method in which a plurality of parameters influencing one another are calculated iteratively in such a way that the values of the parameters converge after a few runs.

For a person skilled in the art, it is a straightforward matter to combine the various exemplary embodiments indicated. For example, a combination of iterative methods with the use of multidimensional look-up tables for determining values is possible, iteration may also be used in the scope of the consistency determination, and the values of additional sensors may readily be integrated into the method.

What is claimed is:

1. A method for determining at least one gas parameter of a flowing gas by using a flow meter,
wherein the flow meter comprises a measurement section having a heating element and at least three temperature sensors, the flowing gas feeding over the heating element and sensors, a. first temperature sensor of the at least three sensors being arranged upstream of the heating element, a second temperature sensor of the at least three sensors being arranged in the region of the heating element, and a third temperature sensor of the at least three sensors being arranged downstream of the heating element, the method further comprising determining, with a calculation unit, at least one of:

a gas parameter as a function of the temperature measurement values of the first, second and third temperature sensors, and two separate gas parameters as a function of the temperature measurement values of the first, second and third temperature sensors and/or the combinations of the temperature measurement values of the first, second and third temperature sensors, wherein the temperature measurement values of the first, second and third temperature sensors are used in the scope of the determination of the gas parameter and the two separate gas parameters, wherein when said two separate gas parameters are being determined the gas parameters are determined repeatedly, the determination being repeated with a different time interval for one of the gas parameters than for the other of the gas parameters.

2. The method according to claim 1, wherein said gas parameter is flow quantity.

3. The method according to claim 1, wherein said heating element is used as said second temperature sensor.

4. The method according to claim 1, wherein as a function of the temperature measurement values of the at least three temperature sensors, three independent gas parameters are determined by the calculation unit as a function of three linearly independent combinations of the temperature measurement values of the first, second and third temperature sensors.

5. The method according to claim 1, further comprising measuring at least one of an ambient temperature and a gas temperature outside the measurement region of the at least three temperature sensors and at a distance from the heating element by using a fourth temperature sensor.

6. The method according to claim 5, wherein said measurement by said fourth temperature sensor is made before entry of the gas into the measurement region of the first temperature sensor or after emerging of the gas from the measurement region of the third temperature sensor.

7. The method according to claim 1, wherein at least one of the gas parameters determined is indicative of a thermal conductivity of the gas or a thermal diffusivity of the gas.

8. The method according to claim 1, wherein a corrected gas parameter indicative of a thermal conductivity is determined as one of the gas parameters as a function of an uncorrected gas parameter indicative of a thermal conductivity and a gas parameter indicative of a flow quantity.

9. The method according to claim 1, wherein a gas parameter indicative of a thermal diffusivity is determined as one of the gas parameters as a function of a gas parameter indicative of a thermal conductivity and a gas parameter indicative of a flow quantity, each of which is determined as a function of at least one instantaneous or previously acquired temperature measurement value.

10. The method according to claim 1, further comprising using a look-up table to determine the gas parameter or at least one of the two separate gas parameters, wherein the values of the look-up table are read as a function of the temperature measurement value, assigned respectively to a dimension of the look-up table, of at least one of the temperature sensors.

11. The method according to claim 10, wherein said look-up table is a multidimensional look-up table and the values of which are read in an interpolated fashion.

12. The method according to claim 1, wherein the temperature measurement values of the temperature sensors do not determine the gas parameter or at least one of the gas parameters uniquely, so that with the same temperature measurement values of all the temperature sensors, a plurality of different values are determined for the gas parameter, and wherein the selection of the determined value is dependent on at least one of:

preceding temperature measurement values of at least one of the temperature sensors;

preceding values of the same gas parameter or the other one of the gas parameters; and known operating conditions of the flow meter.

13. The method according to claim 1, wherein the dependency of the gas parameter on the temperature values at the temperature sensors is approximated by linear or polynomial approximations in order to calculate the gas parameter.

14. The method according to claim 1, wherein the gas parameter or one of the gas parameters is a mixing ratio of at least two gases, a concentration of a gas type, or the gas type of gas.

15. The method according to claim 1, wherein the heating power of the heating element is varied between a first value and at least one second value in order to determine at least one further independent gas parameter.

16. The method according to claim 1, wherein a temperature measurement value of at least one temperature sensor, or a value derived therefrom, is determined at a time at which the heating element is switched off, at least one gas parameter being determined as a function of this temperature measurement value.

17. The method according to claim 1, wherein in the case of a known qualitative composition of the gas, a calorific value of the gas is determined as the gas parameter or at least one of the gas parameters.

18. A flow meter, comprising a calculation unit and a measurement section having a heating element and at least three temperature sensors, over which the gas is fed, at least one first temperature sensor being arranged upstream of the heating element, at least one second temperature sensor being arranged in the region of the heating element, and at least one third temperature sensor being arranged downstream of the heating element, the second temperature sensor being formed in particular by the heating element, wherein the calculation unit is formed in order to carry out the method according to claim 1.

19. The flow meter according to claim 18, further comprising a plurality of second temperature sensors, which are arranged upstream and downstream directly next to the heating element and provide a temperature measurement value individually or together.

20. The flow meter according to claim 18, further comprising an electronic switching unit which connects the first temperature sensor or at least one of the first temperature sensors to the second temperature sensor or at least one of the second temperature sensors and/or to the third temperature sensor or at least one of the third temperature sensors, or the second temperature sensor or at least one of the second temperature sensors to the third temperature sensor or at least one of the third temperature sensors, in such a way that at least one output signal of the switching unit depends on the linearly, by addition or subtraction, and/or by multiplication and/or by division, combined temperature measurement values of the temperature sensors connected by the switching unit, the calculation unit being formed in order to determine the gas parameter or at least one of the gas parameters as a function of the output signal of the switching unit.

21. A method for determining at least one gas parameter of a flowing gas by using a flow meter,
wherein the flow meter comprises a measurement section having a heating element and at least three temperature sensors, the flowing gas feeding over the heating element and sensors, a. first temperature sensor of the at least three sensors being arranged upstream of the heating element, a second temperature sensor of the at least three sensors being arranged in the region of the heating element, and a third temperature sensor of the at least three sensors being arranged downstream of the heating element,
the method further comprising determining, with a calculation unit, at least one of:
a gas parameter as a function of the temperature measurement values of the first, second and third temperature sensors, and
two separate gas parameters as a function of the temperature measurement values of the first, second and third temperature sensors and/or the combinations of the temperature measurement values of the first, second and third temperature sensors,
wherein the temperature measurement values of the first, second and third temperature sensors are used in the scope of the determination of the gas parameter and the two separate gas parameters,
wherein when said two separate gas parameters are being determined, an uncorrected flow quantity is determined as one of the gas parameters from the temperature measurement values at the first and third temperature sensors, and a corrected flow quantity is determined from the uncorrected flow quantity as the other of the gas parameters.

22. A method for determining at least one gas parameter of a flowing gas by using a flow meter,
wherein the flow meter comprises a measurement section having a heating element and at least three temperature sensors, the flowing gas feeding over the heating element and sensors, a first temperature sensor of the at least three sensors being arranged upstream of the heating element, a second temperature sensor of the at least three sensors being arranged in the region of the heating element, and a third temperature sensor of the at least three sensors being arranged downstream of the heating element,
the method further comprising determining, with a calculation unit, at least one of:
a gas parameter as a function of the temperature measurement values of the first, second and third temperature sensors, and
two separate gas parameters as a function of the temperature measurement values of the first, second and third temperature sensors and/or the combinations of the temperature measurement values of the first, second and third temperature sensors,
wherein the temperature measurement values of the first, second and third temperature sensors are used in the scope of the determination of the gas parameter and the two separate gas parameters,
wherein said two separate gas parameters are determined by an iterative method, wherein the first gas parameter of the two separate gas parameters is determined in a first step as a function of the second gas parameter of the two separate gas parameters, and wherein the second gas parameter of the two separate gas parameters is determined in a second step as a function of the first gas parameter.

23. The method according to claim 22, wherein said first gas parameter of the two separate gas parameters is determined in a first step as a function of the temperature measurement value of at least one of the temperature sensors, and said second gas parameter of the two separate gas parameters is determined in a second step as a function of the temperature measurement value of the at least one of the temperature sensors or at least another one of the temperature sensors.

24. A method for determining at least one gas parameter of a flowing gas by using a flow meter,
wherein the flow meter comprises a measurement section having a heating element and at least three temperature sensors, the flowing gas feeding over the heating element and sensors, a first temperature sensor of the at least three sensors being arranged upstream of the heating element, a second temperature sensor of the at least three sensors being arranged in the region of the heating element, and a third temperature sensor of the at least three sensors being arranged downstream of the heating element,
the method further comprising determining, with a calculation mit, at least one of:
a gas parameter as a function of the temperature measurement values of the first, second and third temperature sensors, and
two separate gas parameters as a function of the temperature measurement values of the first, second and third temperature sensors and/or the combinations of the temperature measurement values of the first, second and third temperature sensors,
wherein the temperature measurement values of the first, second and third temperature sensors are used in the scope of the determination of the gas parameter and the two separate gas parameters,
wherein the temperature measurement values of the temperature sensors do not determine the gas parameter or at least one of the gas parameters uniquely, so that with the same temperature measurement values of all the temperature sensors, a plurality of different values are determined for the gas parameter, and
wherein the selection of the determined value is dependent on at least one of:
preceding temperature measurement values of at least one of the temperature sensors;
preceding values of the same gas parameter or the other one of the gas parameters; and
known operating conditions of the flow meter.

25. A method for determining at least one gas parameter of a flowing gas by using a flow meter,
wherein the flow meter comprises a measurement section having a heating element and at least three temperature sensors, the flowing gas feeding over the heating element and sensors, a first temperature sensor of the at least three sensors being arranged upstream of the heating element, a second temperature sensor of the at least three sensors being arranged in the region of the heating element, and a third temperature sensor of the at least three sensors being arranged downstream of the heating element,
the method further comprising determining, with a calculation unit, at least one of:

a gas parameter as a function of the temperature measurement values of the first, second and third temperature sensors, and two separate gas parameters as a function of the temperature measurement values of the first, second and third temperature sensors and/or the combinations of the temperature measurement values of the first, second and third temperature sensors, wherein the temperature measurement values of the first, second and third temperature sensors are used in the scope of the determination of the gas parameter and the two separate gas parameters, wherein the gas parameter or one of the gas parameters is a mixing ratio of at least two gases, a concentration of a gas type, or the gas type of gas.

26. A method for determining at least one gas parameter of a flowing gas by using a flow meter, wherein the flow meter comprises a measurement section having a heating element and at least three temperature sensors, the flowing gas feeding over the heating element and sensors, a first temperature sensor of the at least three sensors being arranged upstream of the heating element, a second temperature sensor of the at least three sensors being arranged in the region of the heating element, and a third temperature sensor of the at least three sensors being arranged downstream of the heating element, the method further comprising determining, with a calculation unit, at least one of;

a gas parameter as a function of the temperature measurement values of the first, second and third temperature sensors, and two separate gas parameters as a function of the temperature measurement values of the first, second and third temperature sensors and/or the combinations of the temperature measurement values of the first, second and third temperature sensors, wherein the temperature measurement values of the first, second and third temperature sensors are used in the scope of the determination of the gas parameter and the two separate gas parameters, wherein a temperature measurement value of at least one temperature sensor, or a value derived therefrom, is determined at a time at which the heating element is switched off, at least one gas parameter being determined as a function of the temperature measurement value.

\* \* \* \* \*

UNITED STATES PATENT AND TRADEMARK OFFICE
CERTIFICATE OF CORRECTION

PATENT NO.        : 9,784,604 B2
APPLICATION NO.   : 14/306586
DATED             : October 10, 2017
INVENTOR(S)       : Christian Schirm Page 1 of 1

It is certified that error appears in the above-identified patent and that said Letters Patent is hereby corrected as shown below:

On the Title Page

(73) Assignee should read:
Diehl Metering GmbH, Ansbach
(DE)

Signed and Sealed this
Sixteenth Day of October, 2018

Andrei Iancu
*Director of the United States Patent and Trademark Office*